United States Patent
Ryan et al.

(10) Patent No.: US 6,414,124 B1
(45) Date of Patent: Jul. 2, 2002

(54) METHODS FOR THE ISOLATION OF PROTEINASE INHIBITOR PROTEINS FROM POTATO TUBERS

(75) Inventors: Clarence A. Ryan, Pullman; Gregory L. Pearce, Palouse, both of WA (US)

(73) Assignee: Washington State Research Foundation, Pullman, WA (US)

( * ) Notice: Subject to any disclaimer, the term of this patent is extended or adjusted under 35 U.S.C. 154(b) by 0 days.

(21) Appl. No.: 09/475,352

(22) Filed: Dec. 29, 1999

Related U.S. Application Data (63) Continuation of application No. PCT/US98/13832, filed on Jul. 1, 1998.
(60) Provisional application No. 60/051,598, filed on Jul. 2, 1997.

(51) Int. Cl.[7] .............................. A23J 1/00; C07K 1/00; C07K 14/00
(52) U.S. Cl. ..................... 530/412; 530/422; 530/370; 530/350
(58) Field of Search .................................. 530/350, 353, 530/370, 412, 422; 426/28, 52; 435/69.1, 213, 219; 536/23.2, 23.6

(56) References Cited

FOREIGN PATENT DOCUMENTS

| EP | 487 480 B1 | 5/1992 | |
|---|---|---|---|
| WO | WO 9401537 A1 | * | 1/1994 |

OTHER PUBLICATIONS

Lin and Jeng, "Trypsin Inhibitor Of Solanum Tuberosum Extraction, Stability, And Change Of Activity During Storage," *Bot. Bull. Academia, Sinica 18*: 109–115, 1977.
Lee, Korean J. Bot. (1989) 32(2);79–88.*
Robyt, John F. and White, Bernard J., Biochemical Techniques: Theory and Practice, Waveland Press (1987) pp. 256–259, 268–270.*
Uchida et al., Sci. Rept. Fac. Agr. Kobe Univ. (1983) 15:357–365.*
Pharmacia Biotech, BioDirectory, (1995) Ch. 9, pp. 217–236.*
Pearce et al., Analytical Biochemistry, (1983) 130:223–225.*

* cited by examiner

*Primary Examiner*—Karen Cochrane Carlson
(74) *Attorney, Agent, or Firm*—SEED Intellectual Property Law Group PLLC (57) ABSTRACT

A rapid and simple method of isolating heat stable proteinase inhibitor proteins from plant tissues such as potato tubers is disclosed. The method comprises three steps. Proteins from potato tubers are extracted in an aqueous/alcohol extraction medium to form an alcohol extract. The alcohol extract is heated to a first temperature then cooled to a second temperature to form an insoluble precipitate phase containing debris and a soluble phase that contains the heat stable proteinase inhibitor proteins. The heat stable proteinase inhibitor proteins are precipitated from the soluble phase by dialysis against a suitable dialysis medium. The precipitated proteins may include a single inhibitor protein, or a mixture thereof.

19 Claims, 6 Drawing Sheets

Fig. 1

Inhibitor II

Fig. 7

METHODS FOR THE ISOLATION OF PROTEINASE INHIBITOR PROTEINS FROM POTATO TUBERS

CROSS-REFERENCE TO RELATED APPLICATION

This application is a continuation under 35 U.S.C. 111(a) of International Application PCT/US98/13832, with an international filing date of Jul. 1, 1998, now pending; which claims the benefit of U.S. Provisional Application No. 60/051,598, filed Jul. 2, 1997; which applications are incorporated herein by reference in their entirety.

TECHNICAL FIELD

This invention is generally directed to methods for the isolation of proteinase inhibitor proteins from plant tissues and, more particularly, to the isolation of heat stable proteinase inhibitor proteins from potato tubers.

BACKGROUND OF THE INVENTION

Tubers from Solanaceous plants such as potato, are an abundant source of a wide range of classes of proteinase inhibitor proteins. Many of these proteins inhibit the activity of digestive proteinases, such as trypsin and chymotrypsin that naturally occur in both insects and mammals. By disturbing the natural digestive process, proteinase inhibitors form part of a plant's natural defense against foraging by herbivores. For the same reason proteinase inhibitors have application in the pest control industry for the control of insects such as fire ants. In addition, because they also inhibit human digestive proteinases, these inhibitors have value in the pharmaceutical industry for the control of obesity and diabetes.

Potato tubers have been a major source for the study and preparation of proteinase inhibitors. Several of the proteinase inhibitors present in potato tubers are of the heat stable variety. Among these are two Kunitz-type proteinase inhibitors having a subunit Mr of about 20 and 20.5 kD that inhibit both trypsin and chymotrypsin (Walsh and Twichell, *Plant Physiol.* 97: 15–18, 1991). The smaller protein is a powerful inhibitor of chymotrypsin, and a weak inhibitor of trypsin. The larger protein is a powerful inhibitor of trypsin. Other heat stable proteinase inhibitors include one with a subunit Mr of about 9.5 kD (designated proteinase inhibitor I) which is a strong inhibitor of chymotrypsin (Melville and Ryan, *J. Biol. Chem.* 247:3445–3453, 1972), and another with a subunit Mr of about 10.5 kD (designated proteinase inhibitor II) which is a strong inhibitor of both chymotrypsin and trypsin (Bryant, Green and Ryan,. Biochemistry 15: 3418–3424, 1976).

Previous methods for preparation of these heat stable proteinase inhibitors have incorporated numerous steps, including: extraction in the presence of dithionate, heat, ammonium sulfate precipitation and chromatography (Walsh and Twichell, *Plant Physiol.* 97: 15–18, 1991; Melville and Ryan, J. Biol. Chem. 247: 3445–3453, 1972; Bryant, Green and Ryan, *Biochemistry* 15: 3418–3424, 1976; Ryan and Kassell, *Methods in Enz.* XIX: 883–889, 1970; Pearce and Ryan, *Anal. Biochem.* 130: 223–225, 1983). Unfortunately these methods are cumbersome, tedious, time consuming, expensive and produce relatively low yields of heat stable proteinase inhibitors. A major problem is that initial extracts form a pasty homogenate with poor flow characteristics resulting in difficulties with subsequent processing steps, especially filtration, ammonium sulfate precipitation and resolubilization. The pasty consistency sometimes requires the use of pressurized filtration during subsequent steps, especially in larger scale extractions (Ryan and Kassell, 1970). Furthermore, the pasty consistency reduces yield because of difficulty in fully recovering material from the paste. These previous methods are also disadvantageous because they require skilled labor to execute and often take several days to complete.

Accordingly, there is a need in the art for a method of isolating proteinase inhibitors from plant tissue, especially potato tubers, that overcomes the problem of the pasty extract, eliminates the need for ammonium sulfate precipitation, is rapid, inexpensive, simple to perform and easy to accomplish on any scale from the laboratory to a large industrial process. The present invention fulfills these needs and provides other related advantages.

SUMMARY OF THE INVENTION

In brief, this invention relates to rapid and simple methods of isolating heat stable proteinase inhibitor proteins from plant tissues containing the same, particularly potato tubers. The method comprises three steps. First, proteins from potato tubers are extracted in soluble form in an aqueous/alcohol extraction medium such as dilute formic acid and 20% ethanol. The presence of the ethanol in the extraction medium converts the otherwise pasty homogenate to a smooth flowing alcohol extract that is easy to manipulate and particularly easy to filter. Second, the alcohol is heated to a first temperature then cooled to a second temperature. Heating in the presence of alcohol denatures most of the unwanted proteins in the alcohol extract, and subsequent cooling leads to formation of a precipitate phase constituting debris and a soluble phase that contains the heat stable proteinase inhibitor proteins. Third, the heat stable proteinase inhibitor proteins are precipitated from the soluble phase by dialysis against a suitable dialysis medium, such as dilute formic acid or water followed by dilute formic acid. The precipitated proteins may be either a single inhibitor protein—proteinase inhibitor II, or a mixture of proteinase inhibitor II and two Kunitz proteinase inhibitors (one most active against trypsin and the other most active against chymotrypsin). The precipitated proteinase inhibitor proteins are free of the bulk of other proteins and other constituents originally present in the tuber.

Whether the precipitated proteins constitute the single inhibitor or the mixture of inhibitors is determined by a single modification. This modification relates to the heating temperature selected for the denaturation step. The single inhibitor may be obtained upon heating to 70° C., cooling to 50° C. followed by dialysis against 0.22% formic acid. The inhibitor mixture may be obtained by heating to 50° C., cooling to room temperature followed by dialysis against water, where the water dialysis is further followed by the addition formic acid to 0.88%.

Excluding dialysis time, the entire method can be performed in less than an hour compared with the days that were required for previous methods. The method is simple, can be performed by unskilled technicians and is amenable to performance on any scale. It avoids the use of expensive ammonium sulfate and chromatography steps, and even the ethanol can be recovered which further reduces the process costs of the method. The method can yield 300 mg of substantially pure proteinase inhibitor proteins from 1 pound of potatoes which is vastly superior to the 150 mg yield of less pure proteins from 100 pounds of potatoes using prior methods.

These and other aspects of the invention are evident upon reference to the following detailed description and Figures.

DETAILED DESCRIPTION OF THE INVENTION

As mentioned above, the present invention is directed to the isolation of one or more heat stable proteinase inhibitor proteins from a plant tissue which contains the same. Potato tubers are a particularly well studied plant tissue which are known to abundantly contain several classes of heat stable proteinase inhibitors. Therefore, in one embodiment of this invention, a method is disclosed for isolation of heat stable proteinase inhibitor proteins from potato tubers. It will also be evident to those skilled in the art that this method can be adapted to the extraction of other proteinase inhibitors from other plant tissues, provided the inhibitors are heat stable and soluble in a solution comprising alcohol and water. In addition to potato tubers, representative tissues may include but are not be limited to, tubers of sweet potatoes or cassava, leaves and fruits of potatoes, tomatoes and legumes, seeds of all plant species, as well as genetically engineered organisms expressing proteinase inhibitor genes.

In the practice of this invention, the method for preparing proteinase inhibitor proteins from plant tissue includes three steps.

In the first step, proteins are extracted from the tissue in an aqueous/alcohol extraction medium to obtain an alcohol extract. "Extraction" means to disrupt cellular structure of the plant tissue so as to release and solubilize cellular contents in the extraction medium. The initial step of extraction is commonly known in the art as "homogenization", which may comprise a disruptive mechanical process such as crushing, grinding, blending, sonicating or other technique. In the present invention the extraction medium is comprised of a solution having an aqueous portion and an alcohol portion. The aqueous portion ideally should be selected to be one that will preferentially solubilize proteinase inhibitors while simultaneously promoting precipitation of unwanted proteins and other macromolecules released from the tissue. Acidic solutions and solutions containing high salt (greater than 0.3 M), have a tendency to precipitate many macromolecules, such as proteins and nucleic acids, whereas several proteinase inhibitors are soluble in the same. Therefore, an embodiment of this invention uses an aqueous portion comprised of dilute formic acid and high salt. Alcohol also has a tendency to precipitate macromolecules and this invention discloses that some proteinase inhibitors remain soluble in solutions containing alcohol. The extraction medium therefore also includes an alcohol portion. The alcohol may be added to the aqueous portion of the extraction medium during or after homogenization of the plant tissue without substantially altering results. In the embodiments disclosed herein, alcohol is added to the aqueous solution during the homogenization process.

Ethanol is used at about 20% v/v in the preferred embodiments described herein. However, other alcohols, including but not limited to, methanol, propanol or phenol may be substituted as well as other water miscible organics. Substitute alcohol(s) may be evaluated by extracting a plant tissue using mediums comprising a variety of alcohols at a variety of concentrations. After centrifuging the debris, measurement of protein levels and specific proteinase inhibitor activities in the supernatant determines an alcohol type and concentration that yields the highest specific activity.

The initial homogenate may be prepared in a solution of dilute formic acid and salt. For example, potato tubers may be homogenized in a blender in a medium having a final concentration of about 0.2% formic acid and 0.3 M NaCl. Ethanol is added during the homogenization process. Addition of ethanol in this manner is particularly useful for extracts prepared from potato tubers because the ethanol changes the consistency of the homogenate from a thick starchy paste to a smooth flowing alcohol extract. This facilitates subsequent manipulations of the alcohol extract, such as removal of coarse debris. In the embodiments described herein, debris is removed by squeezing the alcohol extract through cheesecloth. Other ways to accomplish removal of debris include, but are not limited to, centrifugation, filtration through natural materials like diatomaceous earth, filtration through synthetic filters, extrusion through screen meshes and other techniques.

In the second step, the alcohol extract is heated to a first temperature then cooled to a second temperature. This causes denaturation and precipitation of many unwanted proteins present in the extract and forms an insoluble precipitate phase and a soluble phase. Denaturation is a process that disrupts secondary and tertiary structures of proteins causing them to unfold or otherwise lose their native characteristics. Denaturation may be irreversible if the proteins cannot afterward be made to regain their native characteristics. Alcohol promotes the denaturation of many proteins, especially in the presence of heat. Upon cooling, denatured proteins are susceptible to aggregate to form insoluble precipitates. In the practice of this invention, several proteinase inhibitors are not irreversibly denatured and remain soluble when heated and cooled in the presence of alcohol, while most other proteins precipitate. In particular, the embodiments described herein show that several proteinase inhibitors from potato tuber remain active and soluble in an alcohol extract containing 20% ethanol that has been heated to a first temperature and cooled to a second temperature.

Generally, the alcohol extract should be heated to a first temperature that is hot enough to denature unwanted proteins, but not so hot as to irreversibly denature the proteinase inhibitors. The extract should then be cooled to a second temperature low enough to facilitate aggregation of a precipitate. After cooling, an insoluble precipitate phase containing denatured proteins and other debris will develop.

The precipitate phase can be separated from the remaining soluble phase by centrifugation, filtration or other equivalent method to obtain a clear soluble phase. The soluble phase contains proteinase inhibitor protein.

Selection of the first and second temperatures of the heating step can be determinative of the type of inhibitor obtained because different proteinase inhibitors have different denaturation and/or precipitation properties. In one embodiment using alcohol extracts of potato tubers, the first temperature is 70° C. and the second temperature is 50° C. This yields a preparation containing proteinase inhibitor II. In another embodiment using the same alcohol extract of potato tubers, the first temperature is 50° C. and the second temperature is room temperature. This yields a mixture containing three different inhibitors—proteinase inhibitor II and two Kunitz proteinase inhibitors, one most active against trypsin and the other most active against chymotrypsin.

The method allows selection of the first and second temperatures for the heating step to be modified as needed to obtain best yields of particular types of proteinase inhibitor proteins and for particular varieties of plant tissue. For example, within one embodiment, alcohol extracts from a particular plant tissue can be treated to a series of different first and second temperatures. After centrifuging the debris, measurement of protein levels and specific proteinase inhibitor activities in the supernatant determines the heat treatment that yields the highest specific activity.

The alcohol can be recovered from the soluble phase after heat treating the alcohol extract. In one embodiment, the ethanol may be recovered by evaporation at the second temperature to which the alcohol extract has been cooled. In another embodiment, the alcohol need not be recovered. In either case, the presence or absence of the alcohol will not effect subsequent steps in the method.

In the third step of the method, proteinase inhibitors are recovered from he soluble phase by precipitation via dialysis against a medium that will promote recipitation of the inhibitors, preferably an acid dialysis solution employing a protic acid, such as an organic acid, and more preferably formic acid. The dialysis not only promotes precipitation for recovery of the proteins but also eliminates smaller proteins and other molecules carried over from previous steps. Selection of the dialysis medium is, in part, determined by the proteinase inhibitors to be isolated. In one embodiment, dilute formic acid at about 0.22% is used to recover of proteinase inhibitor II from potato tubers. In another embodiment, tap water is preferred to recover a mixture of three proteinase inhibitors from potato tubers. When tap water is used as the dialysis medium the proteins may be precipitated by the subsequent addition of formic acid to about 0.88%. In either case, the dialysis is across a membrane having a molecular weight cutoff of 12,000–14,000 Daltons. As the salt, residual alcohol and other small molecules present in the soluble extract are removed, a white precipitate will form containing the proteinase inhibitors. In a laboratory scale embodiment, twelve to 24 hours of dialysis is sufficient for complete precipitate formation. However, other methods of dialysis, solute exchange, or precipitation that may yield a better or more rapid recovery of the proteinase inhibitors can be substituted.

The precipitated proteins may be recovered by filtration, centrifugation or other methods. The precipitated proteins contain a mixture of proteinase inhibitor proteins of a variety of degrees of purity. One or more proteinase inhibitor proteins may constitute >90% of the total protein in the precipitate. Such a precipitate may be considered a substantially pure mixture of proteinase inhibitor proteins. The precipitate can be dissolved in a solvent suitable for an intended use or subsequent formulation of the proteinase inhibitors. In the embodiments presented herein, the precipitates are dissolved in 0.1 M ammonium bicarbonate which is suitable for solubilization and subsequent lyophilization—a known method for stable storage of proteinase inhibitors.

The general methodology described herein is suitable for the preparation of a variety of heat stable proteinase inhibitor proteins from a variety of plant tissue provided that the inhibitors are resistant to irreversible denaturation in the presence of alcohol and heat. This method yields mixtures of proteinase inhibitor proteins having various degrees of purity depending upon the specific tissue used, proteinase inhibitors present and on the particular alcohols, temperatures and dialysis medium employed for the method. When optimized for a given tissue, high yields of substantially pure compositions of proteinase inhibitors can be obtained as shown by the examples for potato tuber proteinase inhibitors described below. To this end, the following examples are presented for purposes of illustration, not limitation.

EXAMPLES

Example 1

PREPARATION OF POTATO PROTEINASE INHIBITOR II

One lb. of Russet Burbank potatoes were homogenized in a blender in the presence of 100 ml 0.88% formic acid and 1.5 M NaCl for 2 minutes. While blending, 125 ml of 95% ethanol was slowly added to the homogenate to bring the final ethanol concentration to about 20%. This changed the homogenate from a paste to a liquid mixture which facilitates filtration. Coarse insoluble debris were removed by squeezing the liquid through 8 layers of cheesecloth. The liquid filtrate was collected as the alcohol extract.

The alcohol extract was transferred to an evaporator flask and heated with stirring by immersing the flask in a boiling water bath until the temperature reached 70° C. At that point the flask was attached to flash evaporator with a bath temperature at 50° C. The evaporator was used to recover the ethanol, however, it was not necessary to remove the ethanol to continue with the method. The resulting liquid was centrifuged at 4000×g to remove excess starch and the precipitated insoluble phase which formed, the clear supernatant representing the soluble phase was collected.

The soluble phase was placed in a 12,000–14,000 molecular weight cutoff dialysis band and dialyzed against 10 liters of 0.22% formic acid for at least 12 hours with several changes of the formic acid solution. By this time a white precipitate formed in the bag. The precipitate was pure proteinase inhibitor II which was recovered by centrifugation at 4000×g for 5 minutes. The precipitate was dissolved in 0.1 M ammonium bicarbonate and lyophilized. The yield was approximately 57 mg inhibitor per lb. potatoes. Better yields may be achieved by starting with newly dug potatoes or potato cultivars having higher levels of proteinase inhibitor II.

Figure 1:
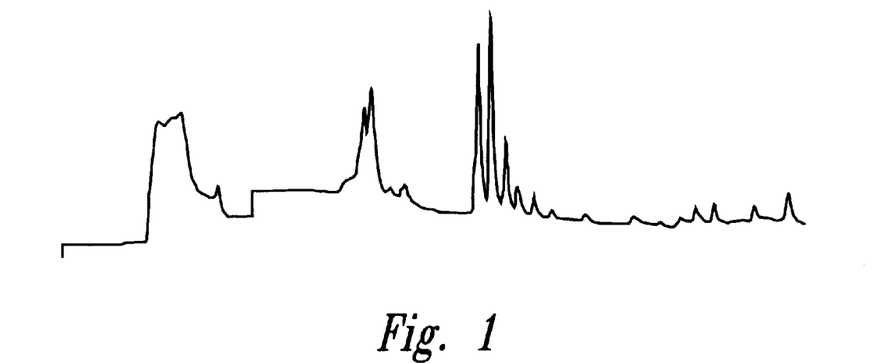
FIG. 1 is the HPLC analysis of a representative heat-treated aqueous/alcohol extract prepared according to this invention before dialysis.
Figure 2:
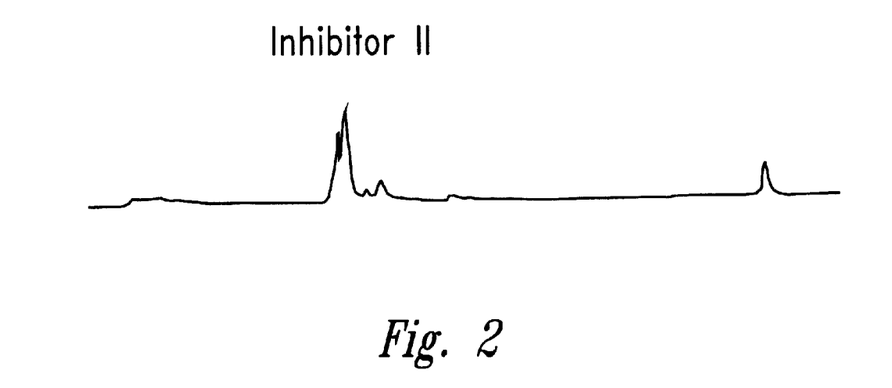
FIG. 2 is the HPLC analysis of a first, post-dialysis, proteinase inhibitor protein mixture prepared according to this invention.

FIGS. 1 and 2 show HPLC analyses of the materials recovered from this procedure. Both figures show spectrophotometeric absorbance at 280 nm of materials eluted from a semipreparative C18 column (Vydac, Catalog #218TP510, 5, 10×250 mm) which was developed at 2 ml/min over 45 minutes with a linear gradient from 20%.solvent A (0.1% trifluoroacetic acid) to 50% solvent B (0.1% trifluoroacetic/ acetonitrile). FIG. 1 shows the soluble material present in the clear soluble phase recovered after heat denaturation of the alcohol extract in step 2 before dialysis. FIG. 2 shows the material present in the precipitate formed after dialysis in step 3. The precipitate was dissolved in solvent A for analysis.

Figure 3:
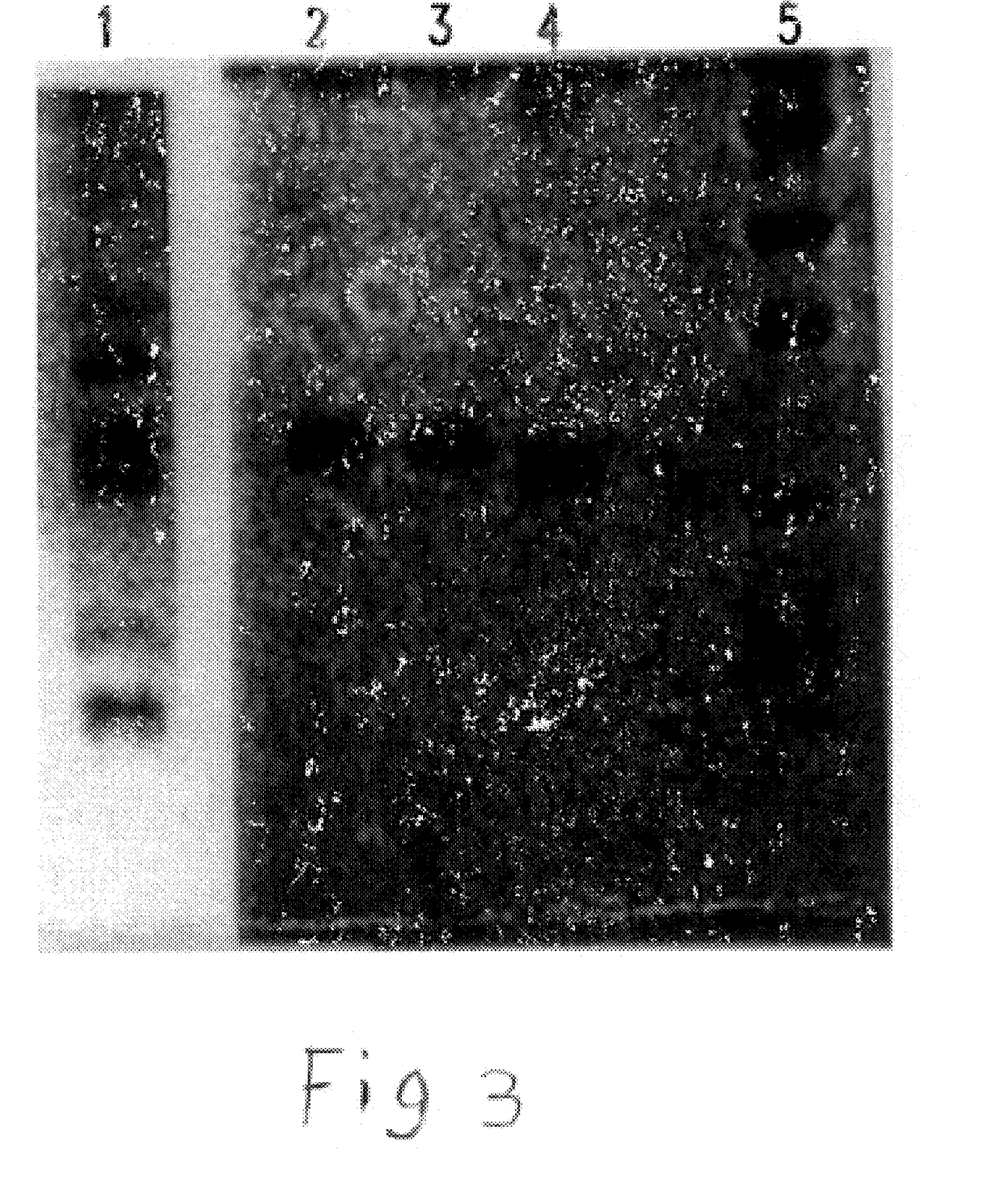
FIG. 3 illustrates gel electrophoresis analysis of a first proteinase inhibitor protein mixture prepared according to this invention.

FIG. 3 shows a gel electrophoresis analysis of the material in peak #1 from the HPLC analysis of FIG. 2. Lane 1 is a sample of the initial potato homogenate prior to the addition of ethanol. Lanes 2, 3, and 4 are samples of the leading, middle, and trailing fractions, respectively, of peak #1. Peak 1 was further subject to immunological analyses which identified the material as potato proteinase inhibitor II.

Figure 4:
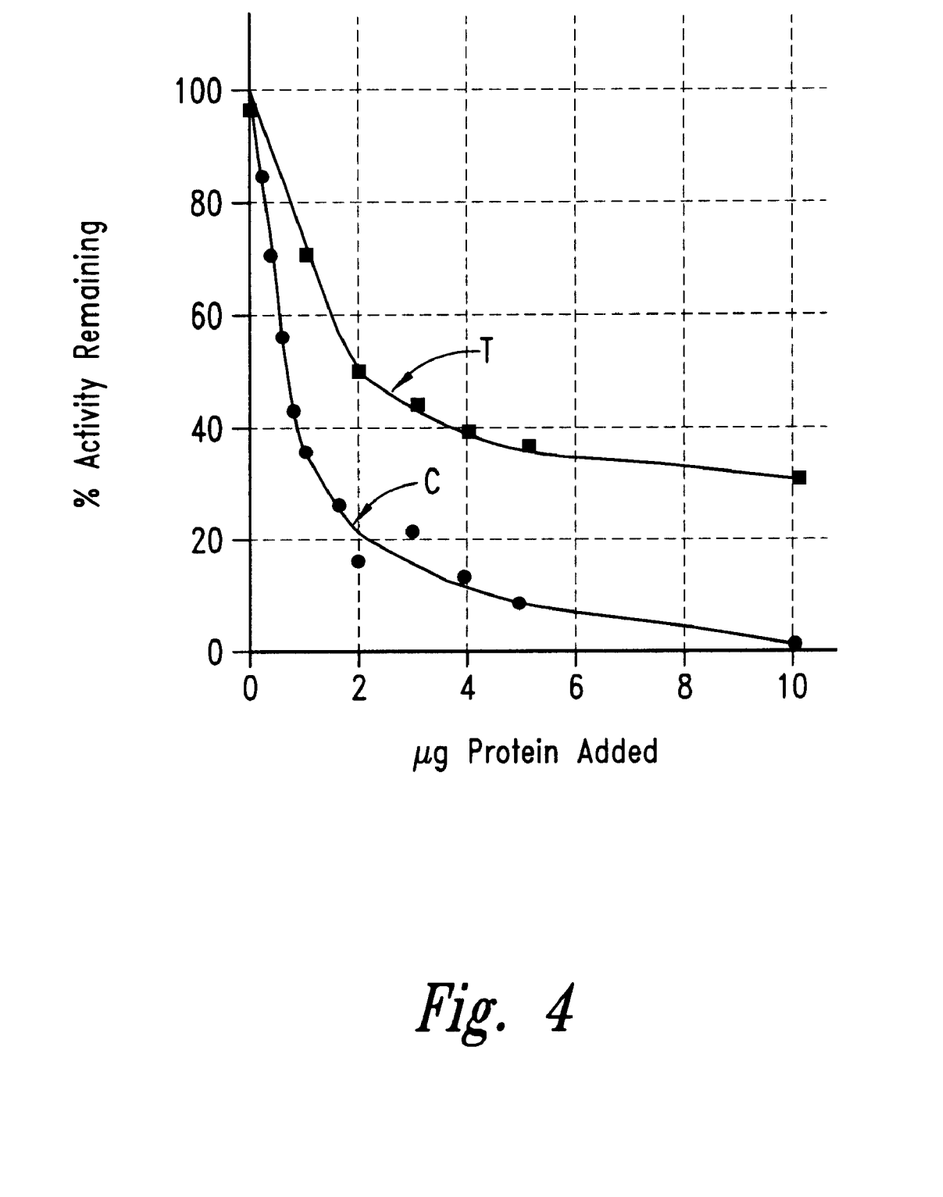
FIG. 4 illustrates proteinase inhibitor activity of a first proteinase inhibitor protein mixture prepared according to this invention.

FIG. 4 shows proteinase inhibitor II activity of peak #1 from FIG. 2. The material was shown to be a strong inhibitor of both trypsin (T) and chymotrypsin (C). For trypsin inhibition, 4.0 µg of the material inhibited 2 µg of trypsin. For chymotrypsin inhibition, 1.4 µg inhibited. 1.5 µg of chymotrypsin. This double-headed inhibitor activity is characteristic of proteinase inhibitor II.

Example 2

PREPARATION OF A MIXTURE OF POTATO PROTEINASE INHIBITORS FROM POTATO

An alcohol extract was prepared as described above in Example 1. The alcohol extract was heated with stirring by immersing the flask in a boiling water bath until the temperature reached 50° C. At that point the flask was immersed in a cold running water bath so that the temperature was reduced to room temperature. The resulting liquid was centrifuged at 4000×g to remove excess starch and the precipitated insoluble phase, the clear supernatant representing the soluble phase was collected.

The soluble phase was placed in a 12,000–14,000 molecular weight cutoff dialysis band and dialyzed against running tap water for 24 hours. After this time either the solution in the bag was adjusted to 0.88% formic acid or alternatively the dialysis solution was adjusted to 0.88% formic acid and dialysis was continued for an additional 4 hours. By this time a white precipitate formed in the bag. The precipitate contained a mixture of proteinase inhibitor II and two Kunitz family proteinase inhibitors as shown in the FIGS. 5 and 6 below. The precipitate was recovered, dissolved and lyophilized as in Example 1. The yield was approximately 300 mg inhibitors per lb. potatoes. Again, better yields may be possible by starting with newly dug potatoes or potato cultivars having higher levels of proteinase inhibitor II.

Figure 5:
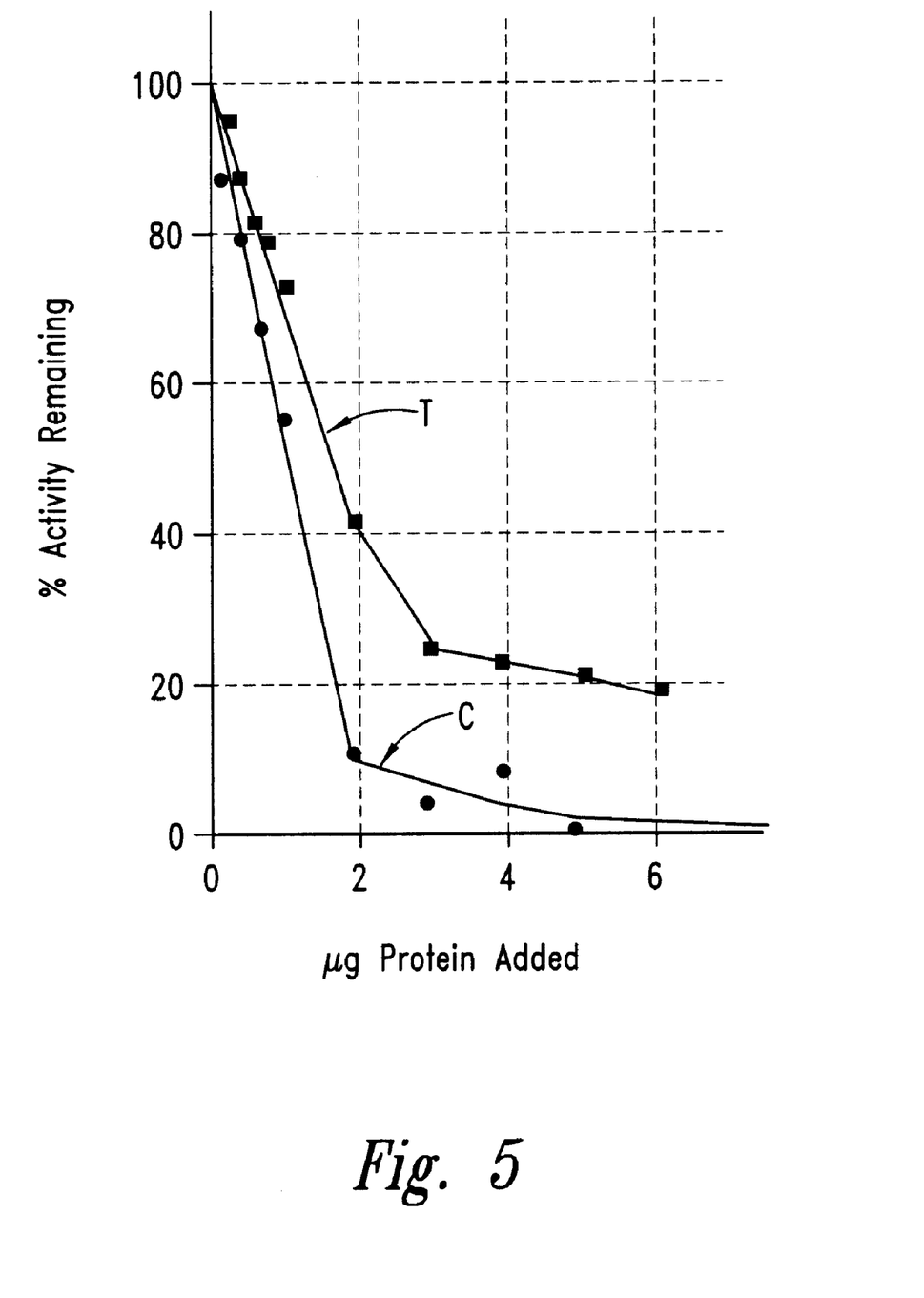
FIG. 5 illustrates proteinase inhibitor activity of a second proteinase inhibitor protein mixture prepared according to this invention.

FIG. 5 shows the proteinase inhibitor activity of the recovered precipitated mixture. The material was found to strongly inhibit both trypsin (T) and chymotrypsin (C). For trypsin inhibition, 3.2 µg of the material inhibited 2.0 µg of trypsin. For chymotrypsin inhibition, 2.2 µg inhibited 1.5 µg of chymotrypsin.

Figure 6:
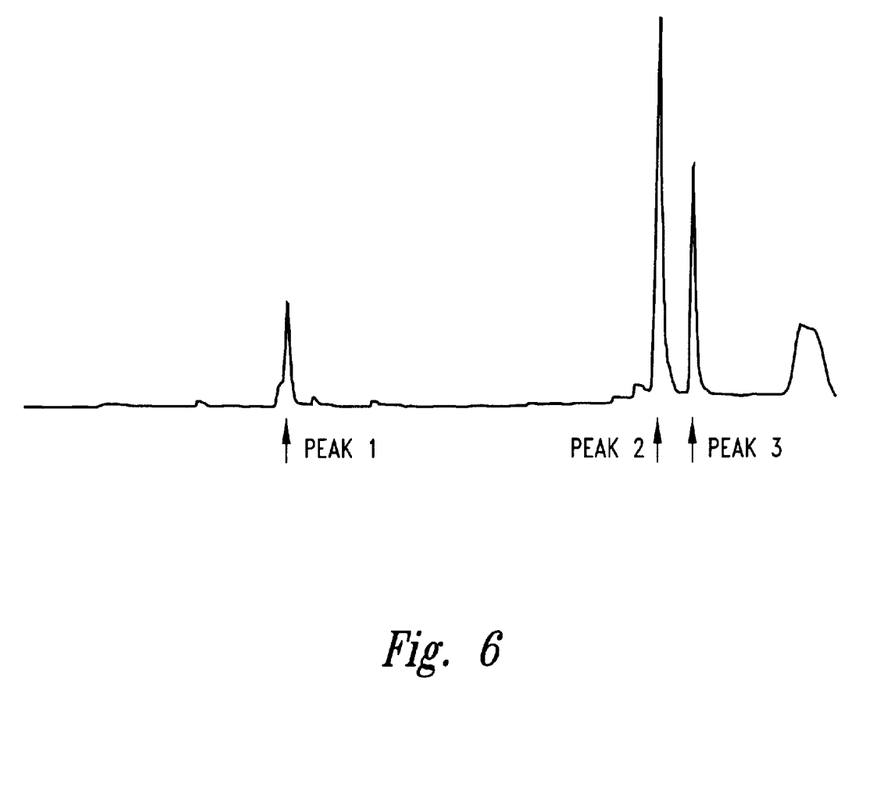
FIG. 6 is the HPLC analysis of a second proteinase inhibitor protein mixture prepared according to this invention
Figure 7:
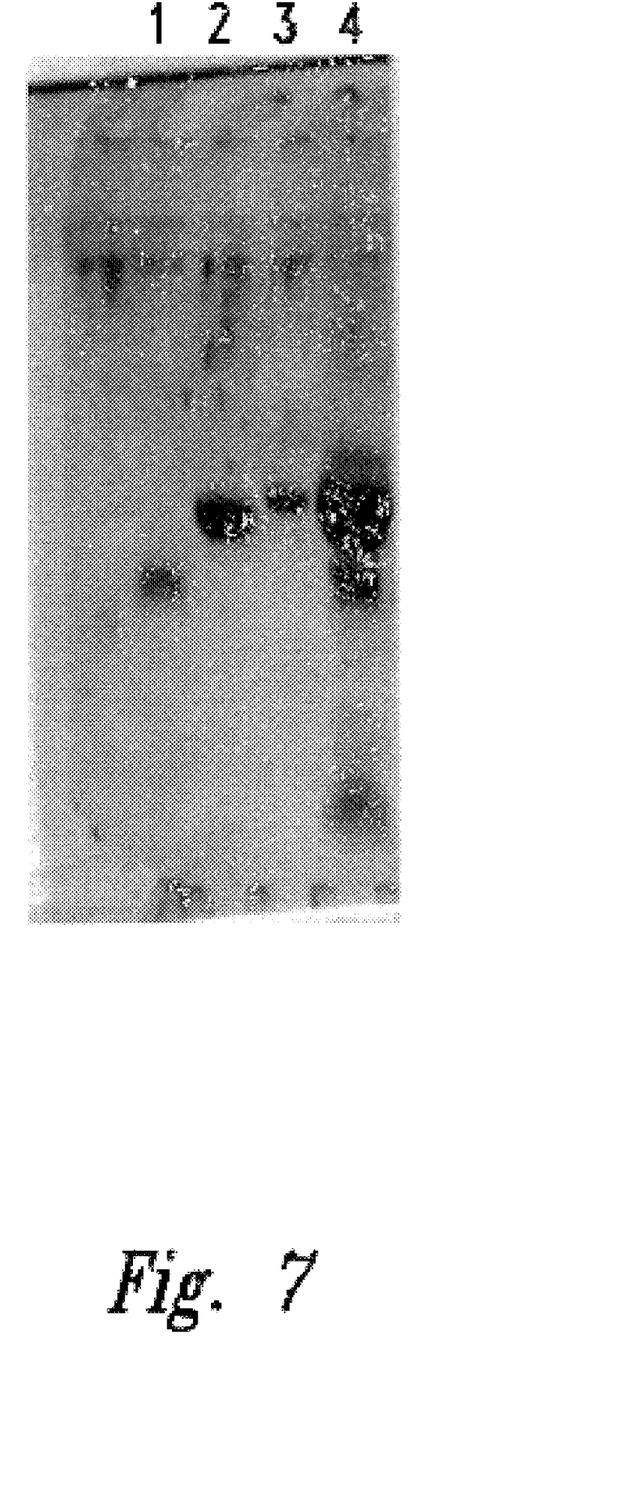
FIG. 7 illustrates gel electrophoresis analysis of a second proteinase inhibitor protein mixture prepared according to this invention

FIG. 6 shows HPLC analysis of the final precipitated material recovered from this procedure. Conditions were the same as described in FIG. 2. The three identified peaks were subject to gel electrophoresis analysis as shown in FIG. 7. Lanes 1, 2, and 3 are the materials from peaks #1, # 2, and #3, respectively, of FIG. 6. As before, immunological analyses identified the material in peak #1 as potato proteinase inhibitor II. The materials from peaks 2 and 3 were subjected to amino acid sequence analysis. The analysis identified peak 2 as a Kunitz-family inhibitor having a powerful chymotrypsin inhibitory activity and a weak trypsin inhibitor. Peak 3 was identified as Kunitz-family inhibitor having a powerful trypsin inhibitor activity.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for obtaining a heat stable proteinase inhibitor protein from plant tissues containing the same, comprising the steps of:

extracting the proteinase inhibitor protein from the plant tissues in an aqueous/alcohol solvent to form an alcohol extract containing a solubilized proteinase inhibitor protein;

heating the alcohol extract to a first temperature of at least 50° C. followed by cooling to a second temperature to form an insoluble precipitate phase and a soluble phase; and precipitating the proteinase inhibitor protein from the soluble phase by dialysis against an acidic dialysis solution. said acid dialysis solution containing formic acid, thereby obtaining a heat stable proteinase inhibitor.

2. The method of claim 1 wherein the plant tissues are potato tubers.

3. The method of claim 1 wherein the proteinase inhibitor protein is potato proteinase inhibitor II.

4. The method of claim 1 wherein the proteinase inhibitor protein is selected from the group consisting of a of potato proteinase inhibitor II, a Kunitz-family chymotrypsin/ trypsin inhibitor having a dominant chymotrypsin inhibitory activity, a Kunitz-family trypsin/chymotrypsin inhibitor having a dominant trypsin inhibitory activity, and mixtures thereof.

5. The method of claim 1 wherein the aqueous/alcohol solvent is comprised of a final concentration of about 0.2% formic acid v/v, about 0.3 M NaCl v/v and about 20% ethanol v/v;

the first temperature is at least 50° C. or above;

the second temperature is room temperature or below; and the aqueous dialysis solution contains about 0.22% formic acid v/v.

6. The method of claim 1 wherein the aqueous/alcohol solvent is comprised of a final concentration of about 0.2% formic acid V/V, about 0.3 M NaCl v/v and about 20% ethanol v/v;

the first temperature is at least 70° C. or above;

the second temperature is at least 50° C. or below; and the aqueous dialysis solution contains about 0.22% formic acid v/v.

7. The method of claim 1 wherein the aqueous/alcohol solvent comprises of about 0.2% formic acid v/v, about 0.3 M NaCl v/v and about 20% ethanol v/v;

the first temperature is at least 50° C.;

the second temperature is at least 27° C. or below; and the aqueous dialysis solution is initially comprised of water; and wherein after a period of dialysis against water, at least one of the soluble phase or the aqueous dialysis solution is adjusted to comprise about 0.88% formic acid v/v.

8. A method for obtaining heat stable proteinase inhibitor protein from potato tubers containing the same, comprising the steps of:

extracting the potato tubers by homogenizing the potato tubers in a medium comprising about 0.2% formic acid and approximately 0.3 M NaCl to form crude extract;

adding about one volume of ethanol to four volumes of crude extract to form an alcohol extract;

filtering the alcohol extract to form a filtered extract;

heating the filtered extract to a first temperature of 50° C. or higher followed by cooling to a second temperature of 27° C. or lower, to form a heat-treated extract containing an insoluble precipitate phase and a soluble phase;

separating the insoluble precipitate phase from the soluble phase by at least one of, filtering the heat-treated extract through a porous filter, or centrifuging the heat-treated extract at about 4000×g for about 5 minutes, to form a clarified soluble phase;

removing impurities from the clarified soluble phase by dialysis using a dialysis membrane having a molecular weight cutoff of approximately 12,000 daltons, against a dialysis medium comprising either tap water, or about 0.2% formic acid v/v, to form a dialyzed extract;

precipitating the proteinase inhibitor proteins from the dialyzed extract by at least one of: including about 0.22% formic acid v/v in the dialysis medium, or adding formic acid to about 0.88% v/v, to form a precipitation mixture;

recovering the precipitated proteinase inhibitor proteins by at least one of, filtering the precipitation mixture through a porous filter, or centrifuging the precipitation mixture at about 4000×g for about 5 minutes, to obtain a mixture of proteinase inhibitor protein, thereby obtaining a heat stable proteinase inhibitor.

9. A heat stable proteinase inhibitor protein obtained according to the method of any one of claims 1–7.

10. A method for obtaining a heat stable proteinase inhibitor protein from tissue containing the same, that includes the step of precipitating the proteinase inhibitor protein by dialysis against an acidic dialysis solution or addition of an acid to a dialyzed soluble phase extract from a soluble phase extract prepared from the tissue wherein said acidic dialysis solution or said acid comprises formic acid.

11. The method of claim 10 wherein prior to dialysis, the soluble extract is heated to a first temperature and cooled to a second temperature to form an insoluble precipitate phase and the soluble phase extract containing the proteinase inhibitor.

12. alcohol is present in the soluble phase extract to form an aqueous/alcohol solvent prior to dialysis or addition of the acid.

13. The method of claim 10 wherein the acid is formic acid or the acidic dialysis solution contains formic acid.

14. The method of claim 13 wherein the acidic dialysis solution contains formic acid at about 0.22% v/v.

15. The method of claim 13 herein dialysis is performed against the soluble phase extract in the absence of acid and formic acid is subsequently added to obtain a solution containing about 0.88% v/v formic acid.

16. The method of any one of claims 10–15 wherein the tissue is a plant tissue.

17. The method of claim 16 wherein the plant tissue is potato tuber.

18. The method of any one of claims 10–15 wherein the tissue is from a genetically engineered organism that expresses a proteinase inhibitor gene.

19. A proteinase inhibitor protein obtained according to the method of any one of claims 9–16.

* * * * *

UNITED STATES PATENT AND TRADEMARK OFFICE
CERTIFICATE OF CORRECTION

PATENT NO.     : 6,414,124 B1
DATED          : July 2, 2002
INVENTOR(S)    : Clarence A. Ryan et al.

It is certified that error appears in the above-identified patent and that said Letters Patent is hereby corrected as shown below:

<u>Column 8,</u>
Line 23, "solution. said acid dialysis solution" should read -- solution, said acid dialysis solution --.
Line 31, "consisting of a of potato" should read -- consisting of a potato --.

Signed and Sealed this

Twenty-fifth Day of February, 2003

JAMES E. ROGAN
*Director of the United States Patent and Trademark Office*